US008212473B2

(12) United States Patent
Kaminska et al.

(10) Patent No.: US 8,212,473 B2
(45) Date of Patent: Jul. 3, 2012

(54) FLEXIBLE POLYMERIC LIGHT EMITTING/CHARGE STORAGE DEVICE AND SYSTEM

(75) Inventors: Bozena Kaminska, Vancouver (CA); Clinton K. Landrock, North Vancouver (CA); Yindar Chuo, Burnaby (CA)

(73) Assignee: Simon Fraser University, Burnaby (CA)

( * ) Notice: Subject to any disclaimer, the term of this patent is extended or adjusted under 35 U.S.C. 154(b) by 82 days.

(21) Appl. No.: 12/762,263

(22) Filed: Apr. 16, 2010

(65) Prior Publication Data

US 2010/0270924 A1    Oct. 28, 2010

Related U.S. Application Data

(63) Continuation-in-part of application No. 12/628,106, filed on Nov. 30, 2009, which is a continuation-in-part of application No. 12/386,789, filed on Apr. 22, 2009.

(51) Int. Cl.
*H05B 33/00* (2006.01)
*H01J 1/62* (2006.01)

(52) U.S. Cl. ............................ 313/506; 313/504; 257/98

(58) Field of Classification Search .................. 313/504, 313/506; 257/98; 315/51
See application file for complete search history.

(56) References Cited

U.S. PATENT DOCUMENTS

| 3,419,760 A | 12/1968 | Raleigh |
| 6,107,452 A * | 8/2000 | Miller et al. ................. 528/422 |
| 6,596,016 B1 | 7/2003 | Vreman et al. |
| 6,872,220 B2 | 3/2005 | Williams et al. |
| 6,882,100 B2 | 4/2005 | Chen et al. |
| 6,896,693 B2 | 5/2005 | Sullivan |
| 7,301,682 B1 | 11/2007 | Puttkammer |
| 7,304,201 B2 | 12/2007 | Holloway et al. |
| 7,347,917 B2 | 3/2008 | Ash et al. |
| 7,351,588 B2 | 4/2008 | Poponin |
| 2004/0111132 A1 | 6/2004 | Shenderova et al. |

(Continued)

FOREIGN PATENT DOCUMENTS

CA     2337787 A1    1/1999

(Continued)

OTHER PUBLICATIONS

Bar-Cohen Y, Bao X, Sherrit S, Shyh-Shiuh Lin, Characterization of the Electromechanical Properties of Ionomeric Polymer-Metal Composite (IPMC), 8 pages, Paper 4695-33, Proceedings of the SPIE Smart Structures and Materials Symposium, EAPAD Conference, San Diego, CA, Mar. 18-21, 2002.

(Continued)

*Primary Examiner* — Joseph L William
(74) *Attorney, Agent, or Firm* — Laurence C. Bonar

(57) ABSTRACT

A light emitting/charge storage device is disclosed. The light emitting/charge storage device includes an organic light emitting diode (OLED) portion and at least one charge storage portion electrically and physically connected therewith. The OLED portion includes a first anode layer, a first cathode layer, and an electroluminescent layer disposed at least partially between the first anode layer and the first cathode layer. The at least one charge storage portion includes a second anode layer, a second cathode layer, and an ionic polymer dielectric layer disposed at least partially between the second anode layer and the second cathode layer, and/or a thin film battery layer. A light emitting/charge storage system is also disclosed. Certain embodiments of the device and system of the invention may provide integrated illumination and charge storage in a unitary stacked layered structure with flexible mechanical characteristics.

20 Claims, 9 Drawing Sheets

U.S. PATENT DOCUMENTS

| | | |
|---|---|---|
| 2006/0030908 A1 | 2/2006 | Powell et al. |
| 2006/0055933 A1 | 3/2006 | Mukai |
| 2006/0217787 A1 | 9/2006 | Olson et al. |
| 2006/0224217 A1 | 10/2006 | Burgmann et al. |
| 2006/0240543 A1 | 10/2006 | Folch et al. |
| 2007/0129613 A1 | 6/2007 | Rochester et al. |
| 2007/0208396 A1 | 9/2007 | Whatcott et al. |
| 2007/0208397 A1 | 9/2007 | Gardner |
| 2007/0223940 A1 | 9/2007 | Smolyaninov et al. |
| 2008/0035736 A1 | 2/2008 | Tompkin et al. |
| 2008/0278728 A1 | 11/2008 | Tetz et al. |
| 2009/0030490 A1 | 1/2009 | Pipe et al. |

FOREIGN PATENT DOCUMENTS

| | | |
|---|---|---|
| CA | 2369744 A1 | 12/2000 |
| EP | 1431062 B1 | 6/2004 |
| EP | 1736323 A1 | 12/2006 |
| WO | WO 2004/056583 A1 | 7/2004 |
| WO | WO 2008/040056 A1 | 4/2008 |
| WO | WO 2008/135502 A1 | 11/2008 |

OTHER PUBLICATIONS

Holger Becker, Claudia Gärtner, Polymer microfabrication technologies for microfluidic systems, Anal Bioanal Chem, 2007, Springer-Verlag.

R. Gordon, M. Hughes, Leathem B., K. L. Kavanagh, A G. Brolo, Basis and Lattice Polarization Mechanisms for Light Transmission through Nanohole Arrays in a Metal Film, 2005, Nano Letters, vol. 5, No. 7 1243-1246, American Chemical Society.

Reuven Gordon, David Sinton, Karen L. Kavanagh, Alexandre G. Brolo, A New Generation of Sensors Based on Extraordinary Optical Transmission, Jun. 21, 2008, Accounts of Chemical research, American Chemical Society.

J Brufau-Penella, M Puig-Vidal, P Giannone, S Graziani, S Strazzeri, Characterization of the harvesting capabilities of an ionic polymer metal composite device, Nov. 27, 2007, Smart Materials and Structures 17 (2008) 015009 (15pp), IOP Publishing Ltd.

F. Carpi, D. De Rossi, Colours from electroactive polymers: Electrochromic, electroluminescent and laser devices based on organic materials, Optics & Laser Technology 38 (2006) 292-305, 2005 Elsevier Ltd.

John W. Franklin, Electromechanical Modeling of Encapsulated Ionic Polymer Transducers, Master of Science Thesis in Mechanical Engineering, 109 pages, Virginia Polytechnic Institute and State University, 2003.

C. Genet, T. W. Ebbesen, Light in tiny holes, Nature, vol. 445, Jan. 4, 2007, Nature Publishing Group.

Bruce Hardwick, Wayne Jackson, Gerard Wilson, Albert W. H. Mau, Advanced Materials for Banknote Applications, Advanced Materials 2001, 13, No. 12-13, Jul. 4, Wiley-VCH Verlag GmbH.

Claudia N. Hoth, Pavel Schilinsky, Stelios A. Choulis, Christoph J. Brabec, Printing Highly Efficient Organic Solar Cells, Nano Letters, 2008, vol. 8, No. 9 2806-2813, American Chemical Society.

Liyu Liu, Suili Peng, Weijia Wen, Ping Sheng, Paper-like thermochromic display, Applied Physics Letters 90, 213508 (2007), American Institute of Physics.

Troy A.E. Loss, Cerrie W. Rogers, Michael 0. Wolf, Composite poly(p-phenylenevinylene)—Nafion thin films, Can. J. Chem. 76: 1554-1558 (1998), NRC Canada.

Franco Moia, New Colour Shifting Security Devices, Optical Security and Counterfeit Deterrence Techniques V, SPIE-IS&T/vol. 5310, SPIE and IS&T, published 2004.

Kenneth M. Newbury, Donald J. Leo, Electromechanical Modeling and Characterizations of Ionic Polymer Benders, Journal of Intelligent Material Systems and Structures, vol. 13—Jan. 2002, SAGE Publications.

Kyung-Won Park, Hyo-Jin Ahn, Yung-Eun Sung, All-solid-state supercapacitor using a Nafion® polymer membrane and its hybridization with a direct methanol fuel cell, Journal of Power Sources 109 (2002) 500-506, 7 pages, Elsevier Science B.V.

John A. Rogers, Zhenan Bao, Kirk Baldwin, Ananth Dodabalapur, Brian Crone, V. R. Raju, Valerie Kuck, Howard Katz, Karl Amundson, Jay Ewing, Paul Drzaic, Paper-like electronic displays: Large-area rubber-stamped plastic sheets of electronics and microencapsulated electrophoretic inks, PNAS,Apr. 24, 2001, vol. 98, No. 9, 4835-4840.

Kwang J. Kim, Mohsen Shahinpoor, A novel method of manufacturing three-dimensional ionic polymer-metal composites (IPMCs) biomimetic sensors, actuators and artificial muscles, Polymer 43 (2002) 797-802, Elsevier Science Ltd.

Kwang J Kim, Mohsen Shahinpoor, Ionic polymer-metal composites: II. Manufacturing techniques, Smart Materials and Structures 12 (2003) 65-79, IOP Publishing Ltd.

Qingjiang Sun, Yongfang Li, Qibing Pei, Polymer Light-Emitting Electrochemical Cells for High-Efficiency Low-Voltage Electroluminescent Devices, Journal of Display Technology, vol. 3, No. 2, Jun. 2007, IEEE.

Jao Van De Lagemaat, Teresa M. Barnes, Garry Rumbles, Sean E. Shaheen, Timothy J. Coutts, Chris Weeks, Igor Levitsky, Jorma Peltola, Paul Glatkowski, Organic solar cells with carbon nanotubes replacing In2O3:Sn as the transparent electrode, Applied Physics Letters 88, 233503, (2006), American Institute of Physics.

Feifei Wang, Yanmin Jia, Jun Wu, Xiangyong Zhao, Haosu Luo, Piezoelectric/electroluminescent composites for low voltage input flat-panel display devices, Applied Physics A 90, 729-731 (2008), Springer-Verlag Alexandre G. Brolo, Shing C. Kwok, Matthew G. Moffitt, Reuven Gordon, Jason Riordon, Karen L. Kavanagh., Enhanced Fluorescence from Arrays of Nanoholes in a Gold Film, J. Am. Chem. Soc. 2005, 127, 14936-14941, American Chemical Society.

Erik Ahlswede, Wolfgang Mühleisen, Mohd Wahinuddin Bin Moh Wahl, Jonas Hanisch, Michael Powalla, Highly efficient organic solar cells with printable low-cost transparent contacts, Applied Physics Letters 92, 143307 (2008), American Institute of Physics.

Il-Seok Park, Sang-Mun Kim, Kwang J Kim, Mechanical and thermal behavior of ionic polymer-metal composites: effects of electroded metals, Smart Materials and Structures 16 (2007) 1090-1097, IOP Publishing.

C Bonomo, L Fortuna, P Giannone, S Graziani and S Strazzeri, A model for ionic polymer metal composites as sensors, Smart Materials and Structures 15 (2006) 749-758, IOP Publishing Yindar Chuo, Clint Landrock, Badr Omrane, Jeydmer Aristizabel, Jasbir N. Patel, Marcin Marzencki, & Bozena Kaminska, Towards Self-Powering Touch/Flex Sensitive OLED Systems, IEEE Sensors Journal (expanded paper from IEEE Sensors 2010 Conference), Jul. 23, 2011, http://ieeexplore.ieee.org/xpls/abs_all.jsp?arnumber=5928374&tag=1.

Yindar Chuo, Badr Omrane, Clint Landrock, Jeydmer Aristizabal, Donna Hohertz, Boris Niraula, Sasan V. Grayli, & Bozena Kaminska, Powering the Future: Integrated, Thin, Flexible Organic Solar Cells with Polymer Energy Storage, IEEE Design and Test of Computers, Jul. 20, 2011, http://www.computer.org/portal/web/csdl/doi/10.1109/MDT.2011.93.

Clinton K. Landrock & Bozena Kaminska, High Temperature Polymer Capacitors for Aerospace Applications, European Design and Automation Association (published in conference proceedings), Mar. 8, 2010, http://portal.acm.org/citation.cfm?id=1871250.

Clint Landrock, High Temperature Capable Ionic Polymer-Metal Composite Capacitors and Power Storage Systems, SAE International (published in conference proceedings), Nov. 2, 2010, http://papers.sae.org/2010-01-1727.

Clinton K. Landrock & Bozena Kaminska, New Capacative Storage Device, PowerMEMS 2009 Conference Proceedings, Dec. 2, 2009, pp. 360-363, PowerMEMS 2009 Conference, Washington DC, USA, Dec. 1-4, 2009.

* cited by examiner

500

FLEXIBLE POLYMERIC LIGHT EMITTING/CHARGE STORAGE DEVICE AND SYSTEM

RELATED APPLICATIONS

This application claims priority benefit to and is a continuation-in-part of previously filed non-provisional U.S. patent application Ser. No. 12/628,106 filed on Nov. 30, 2009, which was a continuation-in-part of previously filed non-provisional U.S. patent application Ser. No. 12/386,789 filed on Apr. 22, 2009, the contents of both of which are herein incorporated by reference in their entirety.

TECHNICAL FIELD

The present invention relates generally to thin organic light emitting devices, and more particularly, to flexible light emitting and charge storage device and system that may be applicable to fields such as phototherapy.

BACKGROUND OF THE INVENTION

Organic light emitting diodes (OLEDs) are currently the subject of rigorous investigative efforts. The applications of OLEDs span from space lighting to controllable displays. Structurally, an organic light emitting diode is typically composed of an organic emissive electroluminescent layer sandwiched between two electrode layers. An electric current is applied to the OLED via the electrodes, causing negatively charged electrons to move into the organic layer from the cathode. Positive charges move in from the anode. The positive and negative charges meet in the center organic layer, combine, and release photons.

The field of phototherapy relates to the use of light exposure to provide; treatments for various ailments; cosmetic procedures; or other health improvements. Examples of physical ailments that may benefit from phototherapy treatments include neonatal jaundice, acne vulgaris, psoriasis, and eczema. Other health conditions such as seasonal affective disorder and adjustments in circadian rhythm for delay sleep phase syndrome have also been demonstrated to benefit from phototherapy treatments. Current technology for phototherapy include the use of lasers, light-emitting diodes (LEDs), fluorescent lamps, and other narrow-band, multi-band, or full spectrum lamp sources.

SUMMARY OF THE INVENTION

Certain features, aspects and examples disclosed herein are directed to a light emitting/charge storage device which may be adapted for a wide variety of applications where illumination may be required, including display, lighting and phototherapy applications. Certain features, aspects and examples are directed to a light emitting/charge storage system that may be adapted for similar applications. Additional features, aspects and examples are discussed in more detail herein.

In accordance with a first aspect, a light emitting/charge storage device is disclosed. The light emitting/charge storage device includes an organic light emitting diode (OLED) portion and at least one polymeric charge storage portion electrically and physically connected with the OLED portion. The OLED portion includes a first anode layer and a first cathode layer, and an electroluminescent layer disposed at least partially between the first anode layer and the first cathode layer. The at least one polymeric charge storage portion includes a second anode layer and a second cathode layer, and an ionic polymer dielectric layer disposed at least partially between the second anode layer and the second cathode layer.

Embodiments of the light emitting/charge storage device of the present invention may include one or more of the following features. In some embodiments, the OLED portion may be disposed at least partially on top of the at least one thin-film polymeric charge storage portion. In certain embodiments, the OLED portion may further include at least one of: a hole transport layer and a hole injection layer, disposed at least partially between the electroluminescent layer and the first anode layer. According to some embodiments, the OLED portion may also include an electron transport layer disposed at least partially between the electroluminescent layer and the first cathode layer.

In some embodiments, the OLED portion may further include an insulating layer disposed at least partially on top of the first cathode layer. According to some embodiments, the light emitting/charge storage device may further include an insulating layer disposed at least partially on top of the second anode layer.

In certain embodiments, the OLED portion may further include a substrate layer, and the first anode layer is disposed at least partially on top of the substrate layer.

In accordance with certain embodiments, the at least one polymeric charge storage portion may include two or more polymeric charge storage units electrically and physically connected to each other. In some embodiments, the two or more polymeric charge storage portions may be stacked substantially on top of each other. In further such embodiments, the light emitting/charge storage device may include an insulating layer disposed at least partially between the two or more polymeric charge storage portions.

In some embodiments, the OLED portion and the at least one polymeric charge storage portion may be electrically and physically connected to each other through patterned conductive vias. In other embodiments, the OLED portion and the at least one polymeric charge storage portion are electrically connected to each other through printed electrical interconnects.

In accordance with an additional aspect, a light emitting/charge storage system is disclosed. The light emitting/charge storage system includes a thin-film layered organic light emitting diode, a thin-film layered charge storage portion electrically and physically connected with the thin-film layered OLED, and circuitry for providing at least one of energy recharge, power regulation and system control functionality to the at least one thin-film layered polymeric capacitor or thin-film layered OLED.

In some embodiments of the present invention, the thin-film layered charge storage portion of the light emitting/charge storage system is capacitive and comprises an anode layer, a cathode layer, and an ionic polymer dielectric layer disposed at least partially between the anode layer and the cathode layer. In other embodiments, the thin-film layered charge storage portion includes a thin film battery.

Embodiments of the light emitting/charge storage system of the present invention may include one or more similar features as described above in connection with the light emitting/charge storage device.

Further advantages of the invention will become apparent when considering the drawings in conjunction with the detailed description.

BRIEF DESCRIPTION OF THE DRAWINGS

The light emitting/charge storage device and light emitting/charge storage system of the present invention will now be described with reference to the accompanying drawing figures, in which.

Similar reference numerals refer to corresponding parts throughout the several views of the drawings.

DETAILED DESCRIPTION OF THE INVENTION

Embodiments of the present invention provide for light emitting/charge storage devices and light emitting/charge storage systems which may be easily manufactured using proven equipment and techniques such as those applied to thin-film structure manufacturing, and which may desirably provide illumination with scalable integrated charge storage capacity and may desirably be produced in a variety of shapes, sizes and configurations. Light emitting/charge storage devices and systems according to embodiments of the invention may advantageously be used in a wide variety of applications where controllable illumination may be required, including display, lighting and phototherapy applications, for example. In phototherapy applications, for example, as compared to traditional phototherapy equipment which may often be limited to rigid, large, bulky, and at best, table-top portable systems, the light emitting/charge storage device and system in at least some embodiments may desirably provide a thin, robust, and mechanically flexible illumination source and integrated charge storage capacity to provide a power source without the requirement for external connections to large battery packs or rigid controller boxes.

Figure 1:
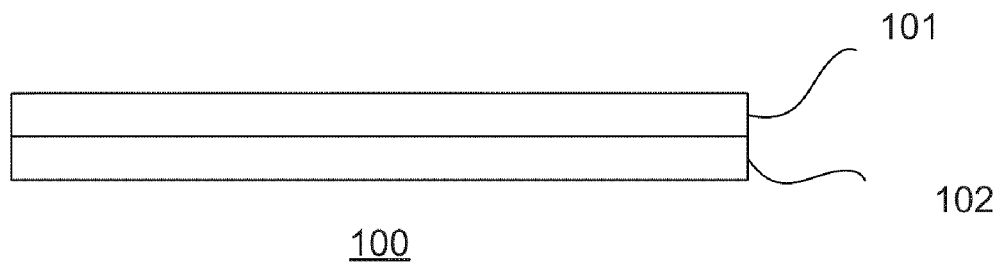
FIG. 1 illustrates a cross-sectional view of an exemplary light emitting/charge storage device according to an embodiment of the present invention.

The present invention will now be further described with reference to the Figures. FIG. 1 illustrates a cross-sectional view of an exemplary light emitting/charge storage device 100 according to an embodiment of the present invention. Light emitting/charge storage device 100 includes an organic light emitting diode (OLED) portion 101 and at least one integrated polymeric charge storage portion, such as an exemplary polymeric charge storage portion 102 electrically and preferably also physically connected with OLED portion 101.

In embodiments of the invention, polymeric charge storage portion 102 and OLED portion 101 may be integrated or physically located adjacent to each other in any suitable manner so long as polymeric charge storage portion 102 may provide electrical energy to power at least a portion of the OLED portion 101 for outputting photonic energy (illumination). In some embodiments, polymeric charge storage portion 102 and OLED portion 101 may be desirably disposed relative to each other in a manner such as to provide illumination and attached charge storage capacity. For example, in the embodiment as shown in FIG. 1, polymeric charge storage portion 102 and OLED portion 101 may be integrated to form a unitary stacked or layered structure. Such a stack/layered structure may be achieved by disposing organic light emitting diode (OLED) portion 101 at least partially on top of integrated or attached polymeric charge storage portion 102, for example. However, the stacking order of organic light emitting diode (OLED) portion 101 and polymeric charge storage portion 102 may be reversed in other embodiments. Such stacking dispositions of polymeric charge storage portion 102 and OLED portion 101 may be advantageous to provide space savings in width and/or planar area of the light emitting/charge storage structure while maintaining a desirably thin profile, for example.

In other embodiments, polymeric charge storage portion 102 and OLED portion 101 may be desirably disposed immediately laterally adjacent to each other. In such embodiments, polymeric charge storage portion 102 and OLED portion 101 may be electrically connected to each other by means of conductive leads or wires for example, or alternatively by conductive vias passing from OLED portion 101 to charge storage portion 102. Such configurations combining laterally adjacent or adjoining polymeric charge storage portion 102 and OLED portion 101 may be advantageous for applications where a thinner profile or form factor than that of a stacking configuration is desired, for example.

Figure 2A:
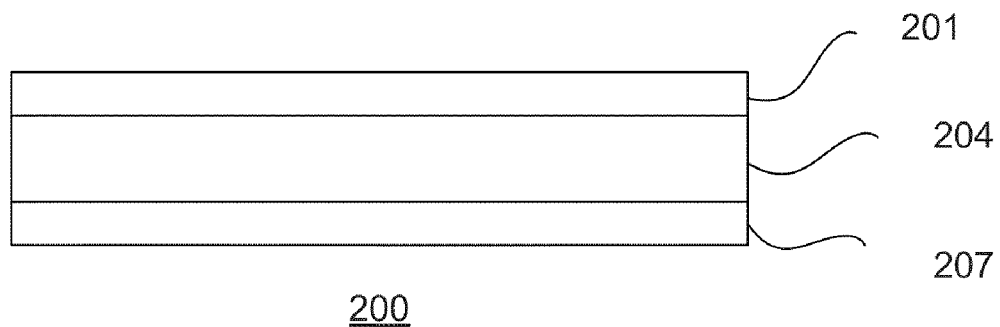
FIGS. 2A-2E illustrate cross-sectional views of the constituent layers in an OLED portion of a light emitting/charge storage device according to various embodiments of the invention.

Each of OLED portion 101 and polymeric charge storage portion 102 may include layers having flexible mechanical qualities that may be advantageous for applications in wearable equipment for phototherapy for example, or other applications where it may be desirable to conform the light emitting/charge storage structure to another object. FIG. 2A illustrates a schematic of an exemplary embodiment of the constituent layers in an OLED portion 200 of a light emitting/charge storage device. OLED potion 200 includes a first anode layer (e.g. anode layer 207), a first cathode layer (e.g. cathode layer 202), and an electroluminescent layer 204 disposed at least partially between anode layer 202 and cathode layer 207.

Cathode layer 202 and anode layer 207 may be made from any suitably electrically conductive material which may be formed as a thin conductive film, so long as at least one of the cathode layer 202 and anode layer 207 is at least partially transparent such that light emitted from electroluminescent layer 204 may transmit in a desired direction. Exemplary such electrically conductive materials for anode layer 207 may comprise metallic materials such as indium-tin-oxide and gold, for example. Exemplary such electrically conductive materials for cathode layer 202 may comprise metallic materials such as indium-tin-oxide, gold, aluminum, calcium, gallium-indium, for example.

Figure 2B:
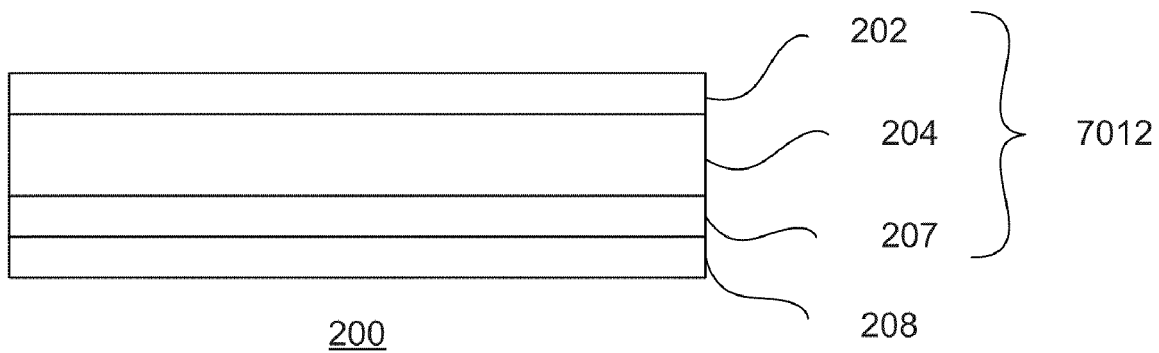

OLED portion 200 may be formed on a suitable substrate, such as substrate 208 illustrated in FIG. 2B, by any one of several suitable known fabrication methods, including physical vapor deposition, screen printing, ink jet printing, in-line fabrication, or the combination thereof, for example. In one embodiment, such as shown in FIG. 2B, anode layer 207 is disposed at least partially on top of substrate layer 208. Emissive layer 204 is disposed at least partially on top of anode layer 207, and cathode layer 202 is disposed at least partially on top of cathode layer 207. In an alternative embodiment, however, an inverted OLED portion 200 may be formed in which cathode layer 202 is disposed on substrate 208 first.

Substrate layer 208 may be formed of any one of several known polymer materials, such as thermoplastic materials, thermoset materials, elastomer materials, or any other suitable flexible materials, such as dense paper based substrates, for example. Examples of known thermoplastic materials may include but are not limited to: polypropylene (PP), polyethylene (PE), polyethylene terephthalate (PET), polyvinyl chloride (PVC), polymethyl methacrylate (PMMA; acrylic), fluorocarbons (PTFE, TFE; Teflon®), polycarbonates (PC), and polystyrene (PS) materials. Examples of known thermoset materials may include but are not limited to: polyimide (PI), and epoxy resins such as SU-8 negative photoresists. Examples of known elastomer materials may include but are not limited to: silicone elastomers, such as polydimethylsiloxane (PDMS) and rubbers.

Figure 2C:
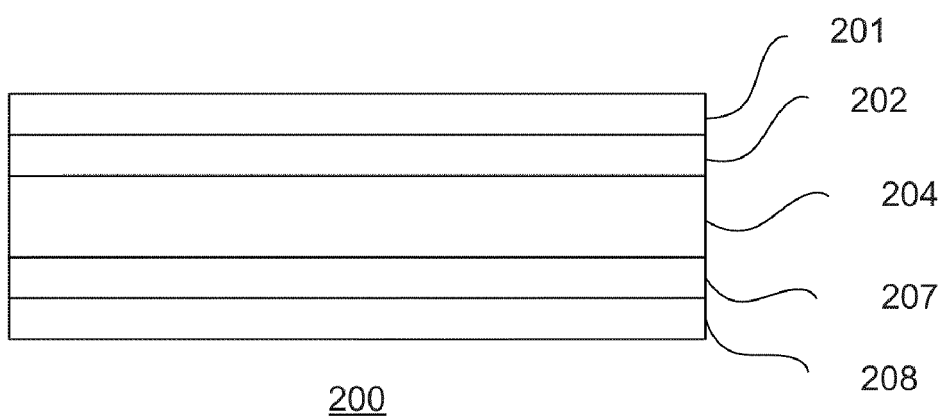

In one embodiment, OLED portion 200 may further include one or more insulating layers. For example, in the embodiment as shown in FIG. 2C, OLED portion 200 may further include an insulating layer 201 disposed at least partially on top of cathode layer 202. Substrate layer 208 may also be selected from a material that serves as an insulating layer. Insulating layers may be advantageously provided to provide insulation to OLED portion 200 from outside ambient environmental conditions, such as small molecule contaminants, air and moisture, for example. In some embodiments, insulating layers may be advantageously provided to further provide mechanical/structural support to OLED portion 200 and/or electrical isolation, for example.

Figure 2D:
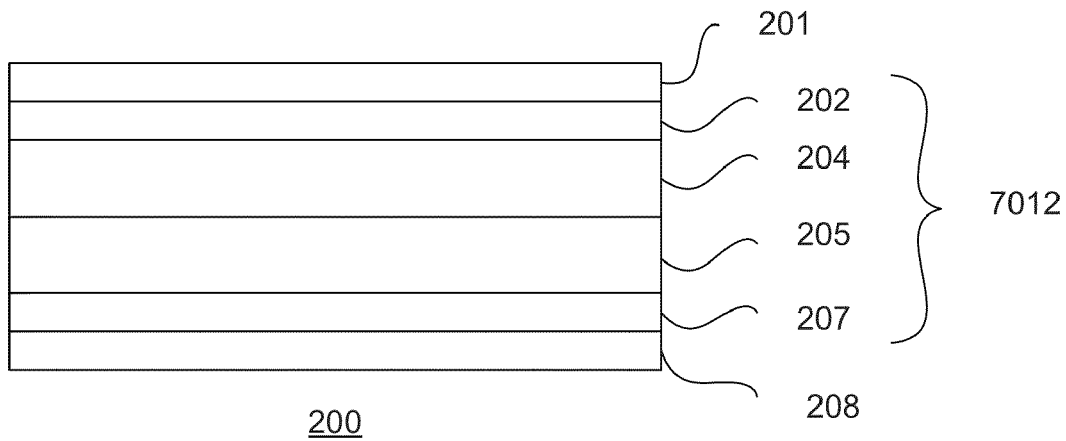
Figure 2E:
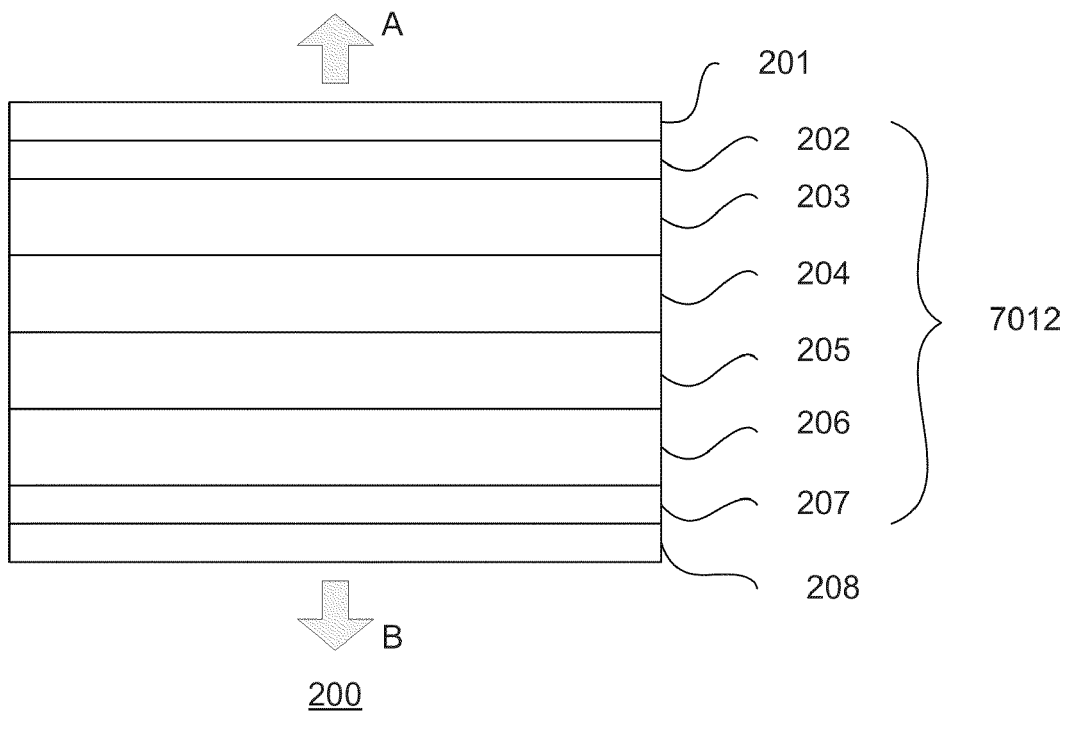

In some embodiments, OLED portion 200 may further include one or more of the following layers: an electron transport layer, a hole transport layer, and/or a hole injection layer. For example, in the embodiment as shown in FIG. 2D, OLED portion 200 may further include a hole transport layer 205 disposed at least partially between electroluminescent layer 204 and anode layer 207. In another embodiment, as shown in FIG. 2E, OLED portion 200 may further include a hole transport layer 205 disposed at least partially between electroluminescent layer 204 and anode layer 207, a hole injection layer 206 disposed at least partially between hole transport layer 205 and anode layer 207, and an electron transport layer 203 disposed at least partially on top of electroluminescent layer 204. Hole transport layer 205 and/or hole injection layer 206 may advantageously be provided to assist in the transfer of positive charges or "holes" from anode layer 201 to electroluminescent layer 203, for example. Similarly, electron transport layer 203 may advantageously be provided to assist in the transfer of electrons from cathode layer 202 to electroluminescent layer 203, for example.

Examples of materials that may be used to form electron transport layer 203 may include but are not limited to: 2,5-Bis(1-naphthyl)-1,3,4-oxadiazole; 2-(4-Biphenylyl)-5-phenyl-1,3,4-oxadiazole; 2-(4-tert-Butylphenyl)-5-(4-biphenylyl)-1,3,4-oxadiazole; 3,5-Bis(4-tert-butylphenyl)-4-phenyl-4H-1,2,4-triazole; 3,5-Diphenyl-4-(1-naphthyl)-1H-1,2,4-triazole; 3-(Biphenyl-4-yl)-5-(4-tert-butylphenyl)-4-phenyl-4H-1,2,4-triazole; bathocuproine; bathophenanthroline; and tris-(8-hydroxyquinoline)aluminum.

Examples of materials that may be used to form hole injection layer 206 may include but are not limited to: 2,3,5,6-Tetrafluoro-7,7,8,8-tetracyanoquinodimethane; 7,7,8,8-Tetracyanoquinodimethane; poly(3,4-ethylenedioxythiophene), bis-poly(ethyleneglycol); poly(3,4-ethylenedioxythiophene), tetramethacrylate; poly(3,4-ethylenedioxythiophene)-block-poly(ethylene glycol); poly(3,4-ethylenedioxythiophene)-poly(styrenesulfonate); poly(thiophene-3-[2-(2-methoxyethoxy)ethoxy]-2,5-diyl); polyaniline (emeraldine salt); and tetracyanoethylene.

Examples of materials that may be used to form hole transport layer 205 may include but are not limited to: 1,3,5-Tris(diphenylamino)benzene; 1,3,5-Tris(2-(9-ethylcabazyl-3) ethylene)benzene; 1,3,5-Tris[(3-methylphenyl)phenylamino]benzene; 1,3-Bis(N-carbazolyl)benzene; 1,4-Bis(diphenylamino)benzene; 4,4'-Bis(N-carbazolyl)-1,1'-biphenyl; 4-(Diethylamino)benzaldehyde diphenylhydrazone; 4-(Dimethylamino)benzaldehyde diphenylhydrazone; 4-(Diphenylamino)benzaldehyde diphenylhydrazone; 4-(Dibenzylamino)benzaldehyde-N,N-diphenylhydrazone; copper(II) phthalocyanine; N,N'-Bis(3-methylphenyl)-N,N'-diphenylbenzidine; N,N'-Di-[(1-naphthyl)-N,N'-diphenyl]-1,1'-biphenyl)-4,4'-diamine; N,N'-Diphenyl-N,N'-di-p-tolylbenzene-1,4-diamine; poly(copper phthalocyanine) dye content; poly[bis(4-phenyl)(2,4,6-trimethylphenyl)amine]; tetra-N-phenylbenzidine; titanyl phthalocyanine dye content; titanyl phthalocyanine β-modification; tri-p-tolylamine; tris(4-carbazoyl-9-ylphenyl)amine; and tris[4-(diethylamino)phenyl]amine.

In some embodiments, electroluminescent layer 204 may comprise any one of several known light-emitting dyes or dopants dispersed in a suitable host material. In further such embodiments, electroluminescent layer 204 may additional comprise polymer hole transport materials. Examples of light-emitting dyes and dopants may include but are not limited to: 5,12-Dihydro-5,12-dimethylquino[2,3-b]acridine-7,14-dione; 8-Hydroxyquinoline zinc; anthracene; anthracene; benz[b]anthracene; benz[b]anthracene; coumarin; dichlorotris(1,10-phenanthroline)ruthenium(II) hydrate; lithium tetra (2-methyl-8-hydroxyquinolinato)boron; perylene; platinum octaethylporphyrin; rubrene; tris(2,2'-bipyridyl)dichlororuthenium(II) hexahydrate; tris(2,2'-bipyridyl-d8)ruthenium (II) hexafluorophosphate; tris(benzoylacetonato) mono (phenanthroline)europium; tris(dibenzoylmethane) mono(1, 10-phenanthroline)europium; tris(dibenzoylmethane) mono (5-amino-1,10-phenanthroline)europium; tris-(8-hydroxyquinoline)aluminum; tris[1-phenylisoquinoline-$C_2$N]iridium(III); tris[2-(4,6-difluorophenyl)pyridinato-$C_2$, N]iridium(III); tris[2-(benzo[b]thiophen-2-yl)pyridinato-$C_3$, N]iridium(III); and tris[2-phenylpyridinato-$C_2$,N]iridium (III). Examples of polymer hole transport and host materials may include but are not limited to: poly(1-vinylnaphthalene), poly(2-vinylcarbazole), poly(2-vinylnaphthalene), poly(9-vinylcarbazole), and poly(N-ethyl-2-vinylcarbazole).

In some embodiments, electroluminescent layer 204 may comprise charge transport and photosensitizing materials. Examples of charge transport and photosensitizing materials may include but are not limited to: 1,4,4-Tetraphenyl-1,3-butadiene; 4-[2-[5-[4-(Diethylamino)phenyl]-4,5-dihydro-1-phenyl-1H-pyrazol-3-yl]ethenyl]-N,N-diethylaniline; 5,12-Bis(phenylethynyl)naphthacene; 9,10-Bis(phenylethynyl)anthracene; 9,10-Di-p-tolylanthracene; 9,10-Phenanthrenequinone; benzo[ghi]perylene; coronene purified by sublimation; julolidine; pentaphene; perylene; phenanthrene sublimed; phenanthridine; phenazine; phenothiazine; pyrazole; quinacridonequinone; quinolin; thioxanthone; triphenylene; violanthrone; and [4-[Bis(2-hydroxyethyl)amino] phenyl]-1,1,2-ethylenetricarbonitrile.

In some embodiments of the present invention, electroluminescent layer 204 may comprise light-emitting polymer materials. Examples of light-emitting polymer materials may include but are not limited to: cyano-Polyphenylene vinylene (CN-PPV) polymers; nitrogen-containing polymers; poly(fluorenylene ehtynylene) (PFE) polymers; poly(phenylene ethynylene) (PPE) polymers; polyfluorene (PFO) polymers and/or co-polymers; polyfluorene-vinylene (PFV) co-polymers; polyphenylene vinylene (PPV) polymers and/or co-polymers; polythiophene polymers and/or co-polymers; and water-soluble light-emitting polymers.

OLED portion 200 may be configured to be either top emissive, bottom emissive, or a combination thereof. To provide photon emission through only the top surface of the OLED portion (the emissive face), the top layer of the OLED portion may be transparent and/or the bottom layer of the OLED portion may be reflective. For example, in the embodiment as shown in FIG. 2E, insulating layer 201 may be transparent and substrate layer 208 may be reflective such that photons emitted from electroluminescent layer 204 pass through insulating layer 201 in the general direction as indicated by arrow A. Alternatively, OLED portion 200 may be configured to be bottom emissive through a reflective top layer and/or a transparent bottom layer. For example, in the embodiment as shown in FIG. 2E, insulating layer 201 may be reflective and substrate layer 208 may be transparent such that photons emitted from electroluminescent layer 204 pass through substrate layer 208 in the general direction as indicated by arrow B.

OLED portion 200 may be selectively configured for varying emission characteristics depending on the application in question. For example, in one embodiment adapted for the phototherapeutic treatment of acne vulgaris, the constituent layers of OLED portion 200 may be selected to produce visible violet light in the wavelength range of about 405 nm to about 420 nm such as to provide total cumulative phototherapeutic doses of 320 J/cm$^2$, for example, wherein the OLED portion 200 may provide an phototherapeutic light output of 20-50 watts/cm$^2$, for example. In another embodiment adapted for the treatment of neonatal jaundice, the constituent layers of OLED portion 200 may be selected to produce radiation in the wavelength range of about 430 nm to about 490 nm at an irradiance level of greater than 30 µW/cm$_2$/nm.

Figure 3:
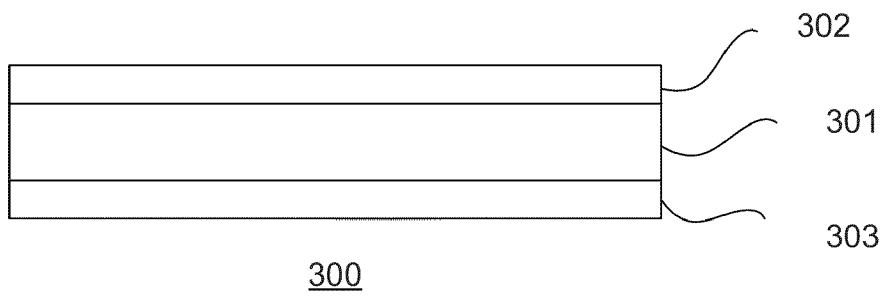
FIG. 3 illustrates a cross-sectional view of an exemplary polymeric charge storage portion according to an embodiment of the invention.

FIG. 3 illustrates a cross-sectional view of a polymeric charge storage portion 300 according to an embodiment of the present invention. The polymeric charge storage portion 300 is preferably provided in the form of thin flexible sheets or layers, and may preferably be manufactured or cut to any desired dimensions as may be required for an intended application, such as one or more of the applications described above, for example. Polymeric charge storage portion 300 includes a second anode layer (e.g. anode layer 302), a second cathode layer (e.g. cathode layer 303), and an ionic polymer dielectric layer 301. In the exemplary embodiment as shown in FIG. 3, anode layer 302 is disposed on top of ionic polymer dielectric layer 301, which is disposed on top of cathode layer 303. However, the placement of anode layer 302 and cathode layer 303 needs not be so limited, and may be varied as long as ionic polymer dielectric layer 301 is disposed at least partially between anode layer 302 and cathode layer 303 to form an ionic polymer metal composite (IPMC) capacitor. In one such variation according to an optional embodiment, at least one of anode layer 302 and/or cathode layer 303 may extend beyond the dielectric layer 301 in at least one dimension of polymeric charge storage portion 300, or vice versa, for example.

The ionic polymer dielectric layer 301 may be formed from any one of several suitable known ionic polymer materials which may be provided as a thin sheet or film, such as fluoropolymer based ionic polymer materials, or polyethylene or polyamide based ionic polymer materials, for example. In particular, a perfluorosulfonic acid (PFSA)/polytetrafluoroethylene (PTFE) copolymer may be used to form ionic polymer dielectric layer 301. Alternatively, a suitable non-hydrated ionic polymer material may be produced in a thin film form suitable to use as ionic polymer dielectric layer 301 such as by spin-coating or otherwise depositing a suitable liquid ionic polymer material and allowing it to dry/cure to form an ionic polymer film, for use as ionic polymer dielectric layer 301. The ionic polymer materials used to form ionic polymer dielectric layer 301 may include cation species that can be tailored for a specific application to achieve a desired energy-storage capacity and charge-discharge performance.

Anode and cathode electrode layers 301 and 302 may be made from any suitably electrically conductive materials which may be formed as a thin conductive film. Exemplary such electrically conductive materials may include but not limited to metallic materials such as gold, silver, platinum, copper, carbon (such as graphitic, polycrystalline or nanocrystalline carbon), aluminum, other known electrically conductive metallic materials, and alloys thereof, and/or conductive polymer materials such as indium tin oxide, polypyrrole (PPy), or other conductive polymers, for example. In one embodiment, anode and cathode electrode layers 301 and 302 may each comprise a film or layer of a suitable electrically conductive material of any suitable desired thickness applied to at least a portion of the surface of ionic polymer dielectric layer 301.

Anode and cathode electrode layers 301 and 302 may be applied to the surface of ionic polymer dielectric layer 301 by any suitable means or method so as to attach, adhere or otherwise suitably join anode and cathode electrode layers 301 and 302 to at least a portion of both major surfaces of ionic polymer dielectric layer 301 to form polymeric charge storage portion 300. In one embodiment, anode and cathode electrode layers 301 and 302 may be formed and applied to ionic polymer dielectric layer 301 by sputtering onto at least a portion of the surface thereof from a source of one or more desired electrically conductive materials, such as in physical sputtering, electronic sputtering, potential sputtering, chemical sputtering, radio frequency (RF) sputtering, DC sputtering, or other known sputtering techniques. In an alternative embodiment, anode and cathode electrode layers 301 and 302 may be independently formed and then attached to ionic polymer dielectric layer 301 such as by adhesion, for example, to form polymeric charge storage portion 300.

In a further embodiment, one or more suitable conductive materials may be applied to at least a portion of the surface of the ionic polymer dielectric layer 301 to form anode and cathode electrode layers 301 and 302 by chemical deposition, vapor deposition, electrochemical deposition such as electroplating, or a combination thereof. In some embodiments of the invention, one or more of the surfaces of the ionic polymer dielectric layer 301 may be prepared prior to the deposition or application of the anode and cathode electrode layers 301 and 302, such as to improve the adhesion, attachment, and/or interface between the anode and cathode electrode layers 301 and 302 and the substrate 1. In one such embodiment, at least a portion of the surface of ionic polymer dielectric layer 301 may be roughened prior to the application of anode and cathode electrode layers 301 and 302, such as by physical surface roughening using abrasive or other suitable roughening means, such as emery cloth or other physical abrasion media, for example. In other embodiments, at least a portion of one or more surfaces of ionic polymer dielectric layer 301 may be roughened prior to application of anode and cathode electrode layers 301 and 302 by alternative means, such as chemical, ion or plasma abrasion, bombardment or ablation methods, for example.

Figure 4:
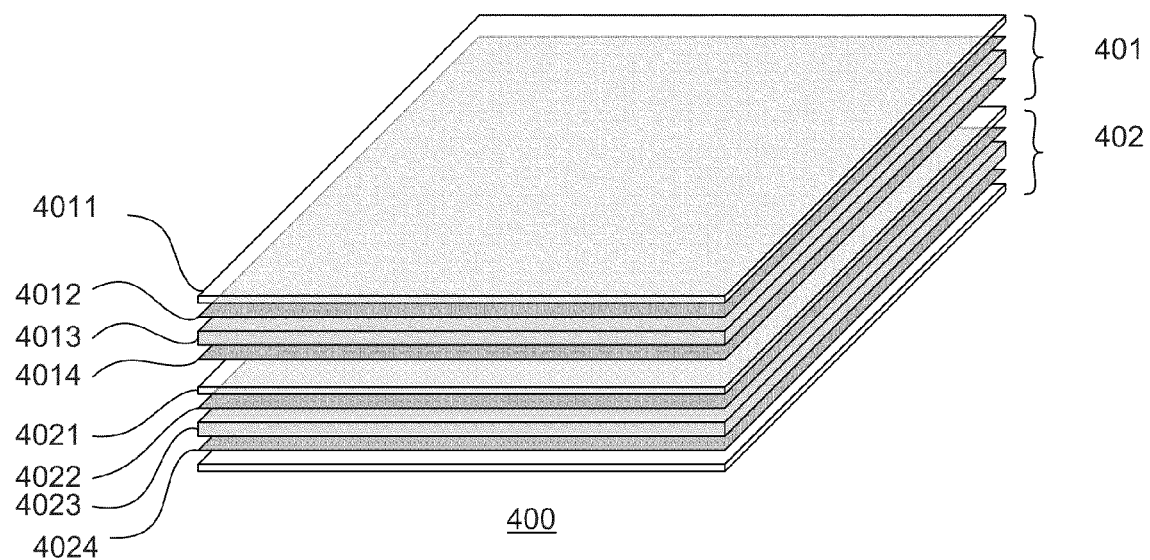
FIG. 4 illustrates a perspective view of a multi-cell ionic polymer metal composite (IPMC) capacitor including two or more polymeric charge storage portions according to an embodiment of the invention.

According to another optional embodiment of the invention as shown in FIG. 4, a multi-cell IPMC capacitor 400 may be provided comprising two or more individual polymeric charge storage portions (e.g. polymeric charge storage portions 401 and 402) electrically connected to each other. Similar to FIG. 3, polymeric charge storage portions 401 and 402 each respectively includes an ionic polymer dielectric layer (4013, 4023) disposed at least partially between a cathode layer (4012, 4022) and an anode layer (4014, 4024). In one such embodiment, two or more polymeric charge storage portions 401 and 402 may be stacked substantially on top of each other with an electrically insulating layer 4021 disposed therebetween where each of polymeric charge storage portions 401 and 402 is electrically connected in parallel to each other in the stack, such as to provide a multi-cell IPMC capacitor of combined capacitive storage capacity, for example. To provide insulation from outside ambient as described above, the top polymeric charge storage portion 401 may additionally include a top insulating layer 4011. In another such embodiment (not shown), multiple polymeric charge storage portions may be connected immediately laterally adjacent to each other and connected in parallel to provide a thin multi-cell capacitor, for example. In further such embodiments, multiple polymeric charge storage portions may be physically combined and electrically interconnected in parallel and/or series connection to provide multi-cell IPMC capacitors, as may be desirable for applications requiring increased capacitive storage capacity and/or redundancy of capacitive storage, for example. Multi-cell IPMC capacitor may advantageously be provided to achieve higher capacity charge storage films as compared to prior art supercapacitors and small film batteries.

Figure 5:
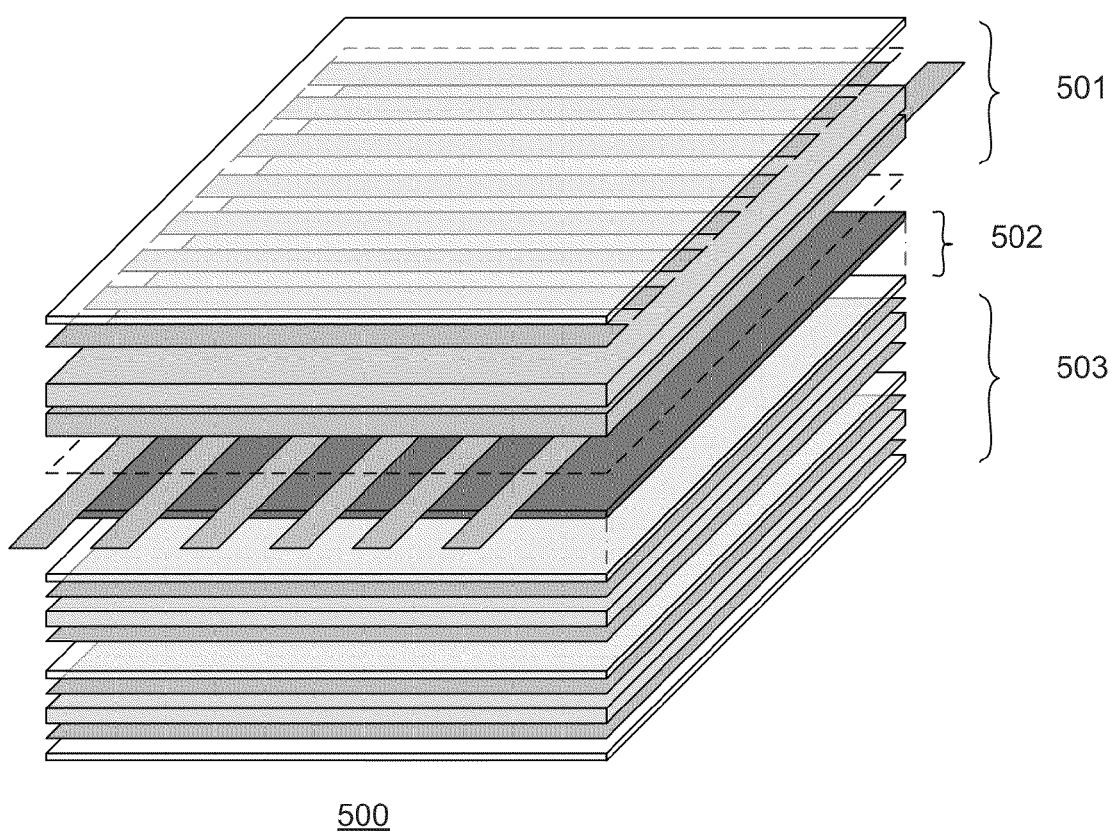
FIG. 5 illustrates a perspective view of an exemplary light emitting/charge storage device arranged in a stacked layered structure according to an embodiment of the invention.

FIG. 5 shows a stacked-layered structure of an exemplary light emitting/charge storage device 500 according to an embodiment of the invention. Light emitting/charge storage device 500 includes an OLED portion 501 electrically connected to a polymeric charge storage portion 503 through layer-to-layer patterned conducting vias which may be formed in one or more interface layers 502. Interface layers 502 separate OLED portion 501 from polymeric charge storage portion 503, and may comprise an OLED substrate layer such as OLED substrate layer 208 described in connection with FIGS. 2B-2E, and may additionally comprise an insulating layer disposed on top of polymeric charge storage portion 503 to provide the functions as described in connection with FIG. 4.

In one embodiment, OLED portion 501 and polymeric charge storage portion 503 may desirably be fabricated in an exemplary single linear process such as a multi-layer deposition process or a roll-to-roll process for example, to form light emitting/charge storage device 500 in a stacked-layered structure. In another embodiment, OLED portion 501 and polymeric charge storage portion 503 may be fabricated in parallel or by independent processes, then conjoined together after to form an integrated light emitting/charge storage device 500.

The light emitting/charge storage device 500 may be designed and fabricated to a desired thickness depending on the application in question. In one embodiment, the thickness of OLED portion 501 may range from about 0.5 µm to about 10 µm, and the thickness of polymeric storage portion 503 may range from about 25 µm to about 250 µm. The thickness of interface layer 502 may range from about 50 µm to about 250 µm. For applications that require structural rigidity and high power capacity for example, the thickness of light emitting/charge storage device 500 may be desirably increased.

Figure 6A:
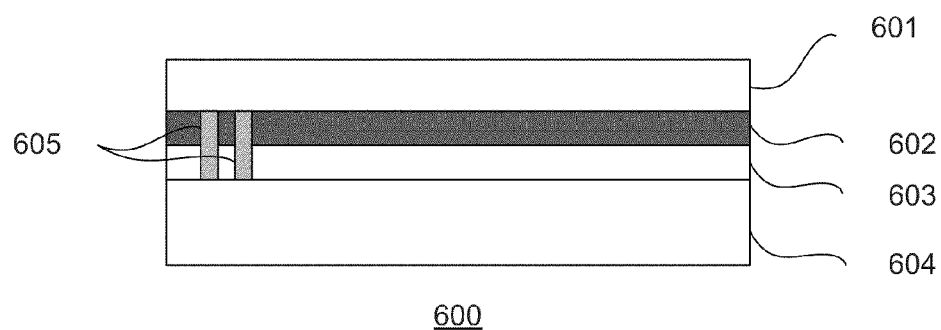
FIGS. 6A and 6B illustrate cross-sectional views of the electrical connections between an OLED portion and a polymeric charge storage portion through electrically conducting vias according to different embodiments of the invention.
Figure 6B:
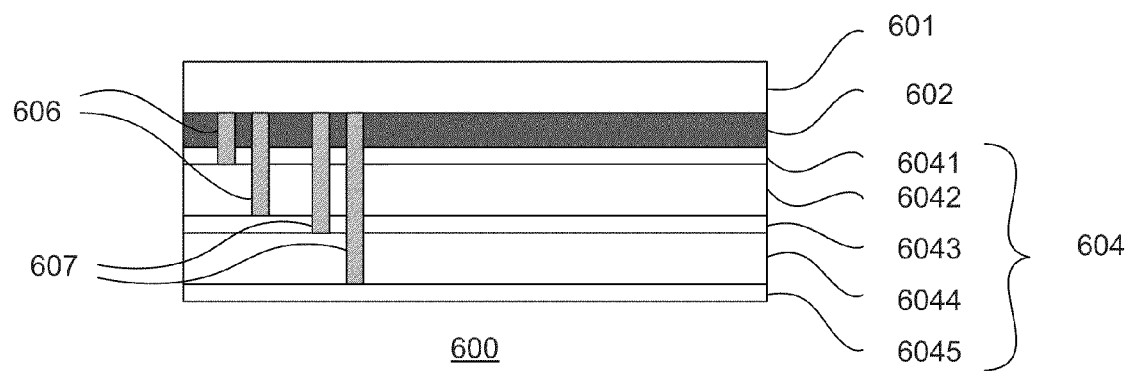

FIGS. 6A and 6B show two exemplary embodiments of electrical connections between an OLED portion and a polymeric charge storage portion through electrically conducting via configurations, such as may be patterned by a suitable multi-layer deposition process, for example. As shown in FIG. 6A, electrically conducting vias 605 are patterned through interface layers, defined by a top insulating layer 603 of (at least one) polymeric charge storage portion 604 and a substrate layer 602 of OLED portion 601, to electrically connect the top surface of polymeric charge storage portion 604 to the bottom surface of OLED portion 601. FIG. 6B shows an alternative embodiment illustrating a configuration wherein an OLED portion 601 is electrically connected to two or more polymeric charge storage portions 604 of a light emitting/charge storage device 600 through layer-to-layer conducting vias 606 and 607. Polymeric charge storage portions 604 includes a top insulating layer 6041, a first polymeric charge storage portion 6042, an intermediate insulating layer 6043, a second polymeric charge storage portion 6044, and a substrate layer, such as carrier substrate layer 6045. As compared to FIG. 6A, polymeric charge storage portions 604 in FIG. 6B are treated as separate functional layers including two capacitive cells: first polymeric charge storage portion 6042 and second polymeric charge storage portion 6044. Therefore, two sets of electrically conductive vias 606 and 607 are patterned to connect the two functional polymeric charge storage layers (first polymeric charge storage portion 6042 and second polymeric charge storage portion 6044) to OLED substrate layer 602 respectively.

Figure 7:
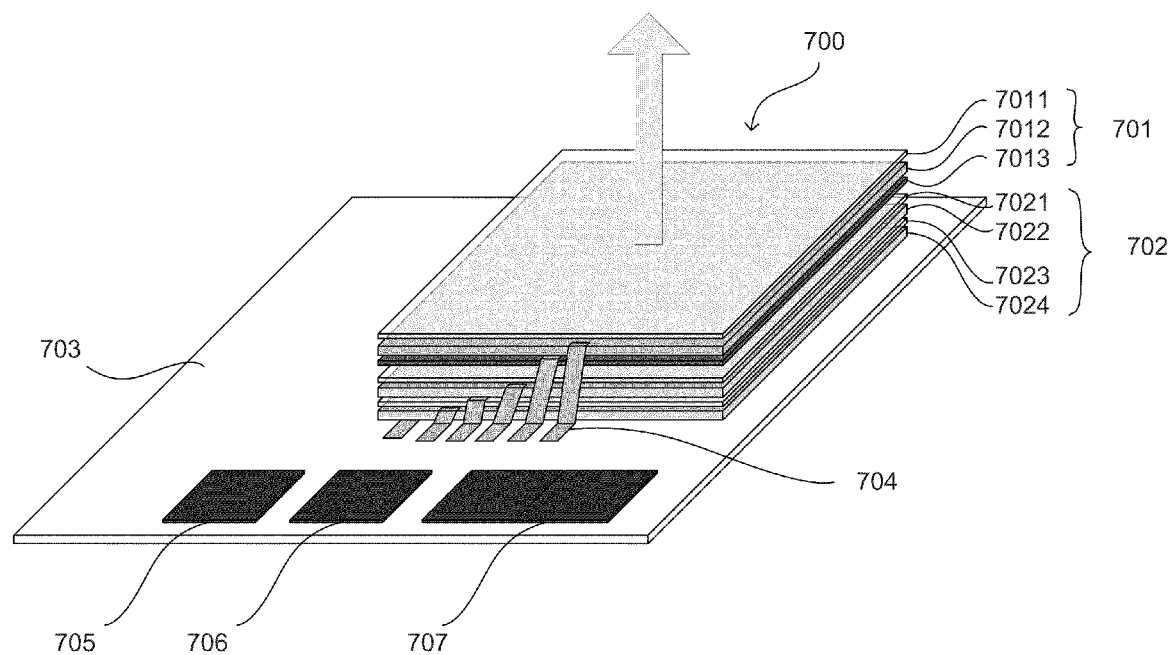
FIG. 7 illustrates a perspective view of the electrical connections between an OLED portion and a polymeric charge storage portion through printed layer-to-layer interconnects according to an embodiment of the invention.

In an alternative embodiment, the OLED portion may be electrically connected to the polymeric charge storage portion through printed layer-to-layer interconnects. As shown in FIG. 7, a light emitting/charge storage device 700 includes an OLED portion 701 and at least one charge storage portion, such as a two-cell IPMC capacitor comprised of two charge storage portions 702 which may be disposed in a vertical stack. Stacked charge storage portions 702 may include a first charge storage portion 7022 disposed substantially on top of a second charge storage portion 7024 with an intermediate insulating layer 7023 disposed therebetween. OLED portion 701 may be disposed on top of charge storage portions 702 to form a unitary stacked-layered configuration as shown whereby charge storage portions 702 may provide in-situ charge storage to power OLED portion 701. An additional insulating layer 7021 may be provided to separate stacked charge storage portions 702 from OLED portion 701. OLED portion 701 may include OLED active layers 7012 defined by an electroluminescent layer sandwiched between two electrode layers and may optionally include additional charge transport layers (not shown), as described above in connection with FIGS. 2A-2E. OLED active layers 7012 may be formed on a substrate layer 7013. To provide insulation, a top insulating layer 7011 may be disposed (at least partially) on top of OLED active layers 7012.

As further shown in FIG. 7, light emitting/charge storage device 700 may be disposed on top of a substrate layer, such as a flexible polymer carrier substrate layer 703. Each of the electrode layers of OLED portion 701 and of stacked polymeric charge storage portions 702 may be extended to be in electrical contact with carrier substrate layer 703 through patterned or printed lay-to-layer electrode interconnects, such as printed interconnects 704. Through exemplary printed interconnects 704, the aforementioned electrode layers may also be further electrically connected with and routed to various other optional circuitry or electronics, which may include an energy recharge circuit 705, a power regulation circuit 706, and a system control circuit 707 for example, such as to advantageously provide respective energy recharge, power regulation, and control of light emitting/charge storage device 700, for example, such as further described in reference to FIG. 8.

Figure 8:
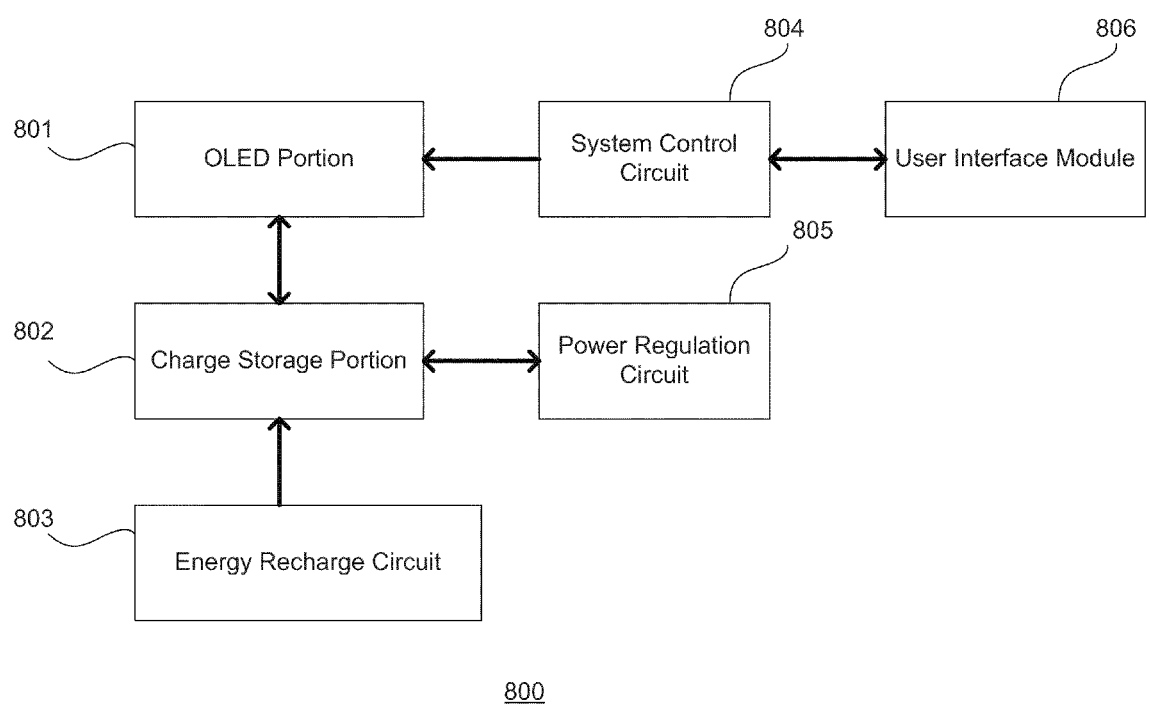
FIG. 8 is a schematic view of a light emitting/charge storage system according to an embodiment of the invention.

FIG. 8 is a schematic of a light emitting/charge storage system 800 according to an embodiment of the invention. Light emitting/charge storage system 800 includes a thin-film layered organic light emitting diode (OLED) portion 801 and a thin-film layered charge storage portion 802 electrically and physically connected to each other. In one embodiment, thin-film layered charge storage portion 802 may comprise a capacitive element, which may comprise an anode layer, a cathode layer, and an ionic polymer dielectric layer disposed at least partially between the anode and cathode layers such as in the manner as described in connection with FIG. 3. In an alternative embodiment, thin-film layered charge storage portion 802 may comprise a thin-film battery. Descriptions of the methods of fabrication and the structure of a thin-film battery are known in the art. An exemplary thin-film battery may comprise a solid-state, thin-film lithium battery constructed in an anode/solid electrolyte/cathode geometry. Preferred solid electrolytes may include materials that are desirably solid at room temperature, electrically insulative and ionically conductive. Examples of solid electrolytes include metallic salts and vitreous solid compositions.

Light emitting/charge storage system 800 further includes an energy recharge circuit 803 which may be connected to an external power recharge source (not shown) through wired or wireless electrical connection. Energy recharge circuit 803 may be electrically connected to charge storage portion 802 to advantageously provide energy recharge thereof. In one embodiment, light emitting/charge storage system 800 may further include a power regulation circuit 805 electrically connected to polymeric charge storage portion 802 to maintain the voltage and current output therefrom for powering OLED portion 801 at desirable levels specific for a particular application. In another embodiment, light emitting/charge storage system 800 may further include a system control circuit 804 electrically connected to OLED portion 801 to control the illumination characteristics thereof, such as illumination intensity, illumination duration, illumination wavelengths and/or patterns and on-off control, for example. In one embodiment, system control circuit 804 may additionally be electrically connected wired or wirelessly to a user interface module 806 for receiving user control requests therefrom and outputting corresponding control signals to control OLED portion 801.

Circuitry such as energy recharge circuit 803, system control circuit 804, and power regulation circuit 805 for controlling and operating OLED portion 801 and polymeric charge storage portion may be implemented with any one of several suitable known techniques. For example, those circuits may be provided as built-in thin-film transistor layers integrated with OLED portion 801 and charge storage portion 803 in a unitary stacked layered structure to form light emitting/charge storage system 800. Circuitry may also be implemented as unpackaged chips integrated with the substrate layer, such as shown in FIG. 7, or as packaged modules populated on top of a substrate layer, for example.

Figure 9:
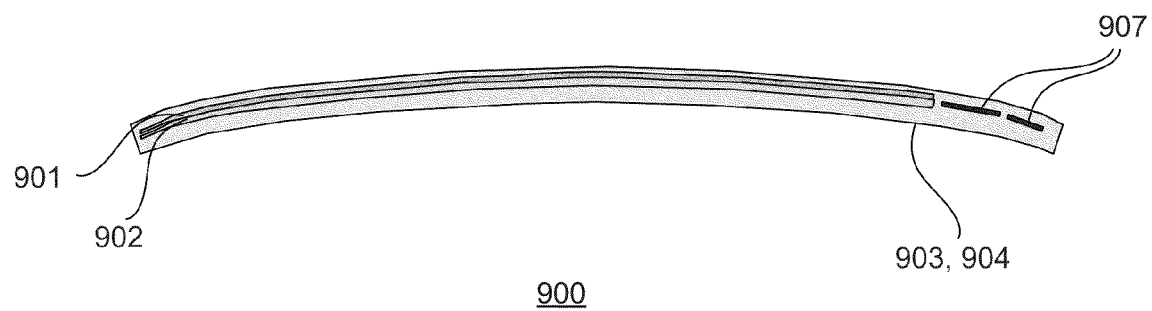
FIG. 9 is a cross sectional view of a light emitting/charge storage system according to another embodiment of the invention.

FIG. 9 shows a cross sectional view of a light emitting/charge storage system 900 according to an embodiment of the invention that may be suitable for phototherapy application, for example. As shown in FIG. 9, light emitting/charge storage system 900 may provide fully integrated illumination and charge storage, including an OLED portion 901 which may be electrically connected with and physically disposed on top of a polymeric charge storage portion 902. Light emitting/charge storage system 900 may additionally comprise circuitry 907, which may include system control, power regulation, and energy recharge capabilities as described in connection with FIGS. 7 and 8. Circuitry 907 may be formed together with OLED portion 901 and polymeric charge storage portion 902 on a substrate layer, such as a flexible polymer carrier substrate layer 903, in a manner similar to that as described in connection with FIG. 7. In some embodiments, at least a portion of OLED portion 901, polymeric charge storage portion 902, carrier substrate layer 903, and circuitry 907 may be hermetically sealed in an encapsulant 904, which may desirably provide light emitting/charge storage system 900 as a stand-alone system-in-package requiring no connection to external battery or power sources.

Encapsulant 904 may be mechanically flexible in at least one direction, and may comprise any one of several known polymer materials, such as thermoplastic materials, thermoset materials, elastomer materials, or any other suitable flexible materials, for example. Examples of known thermoplastic materials may include but are not limited to: polycarbonates (PC), polyethylene terephthalate (PET), polyethylene (PE), and polypropylene (PP) materials. Examples of known thermoset materials may include but are not limited to: polyimide (PI) and epoxy resins, such as SU8 negative photoresist. Examples of known elastomer materials may include but are not limited to: rubbers, and silicone elastomers, such as polydimethylsiloxane (PDMS). In some embodiments, encapsulant 904 may be formed of the same material as carrier substrate layer 903, such as in the embodiment as shown in FIG. 9.

Figure 10:
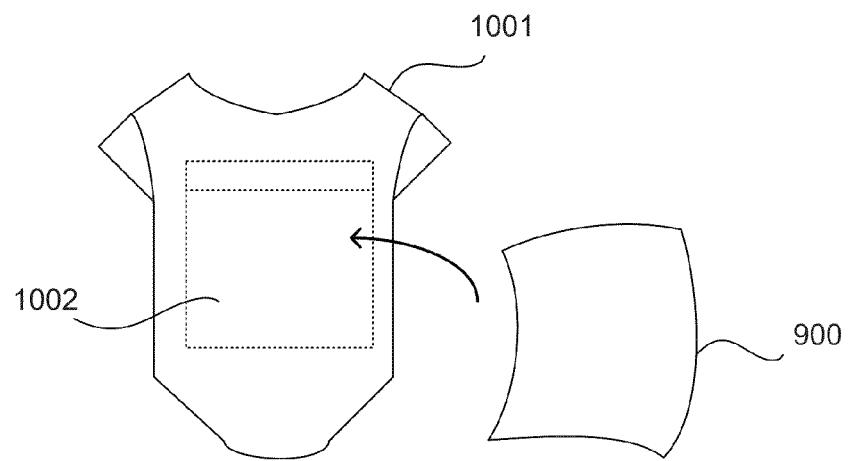
FIG. 10 is a schematic view of the light emitting/charge storage system 900 of FIG. 9 adapted for application in the phototherapeutic treatment of jaundiced infants.

In some embodiments, the components of light emitting/charge storage system 900 may advantageously be formed of polymer materials that may be suitable for a variety of applications that may require high mechanically flexibility, such as wearable phototherapy and lighting applications, for example. In one particular embodiment, suitable polymer materials may be selected to provide light emitting/charge storage system 900 with thin, robust, and mechanically flexible qualities. FIG. 10 shows a schematic view of the light emitting/charge storage system 900 of FIG. 9 adapted for retrofitting in wearable clothing 1001 for the phototherapeutic treatment of jaundiced infants. In one embodiment, light emitting/charge storage system 900 may be inserted into a pocket 1002 formed on the back side of wearable clothing 1001, for example. In other phototherapy applications, light emitting/charge storage system 900 may be embedded, integrated, and/or removably adapted for use in patches, blankets, bandages, masks, garments, bed sheets, linings of tanning beds and incubators, for example.

It is to be noted that, as will be understood by a person of ordinary skill in the art, the light emitting/charge storage device according to embodiments of the invention may also be hermetically sealed in an encapsulant and adapted for similar applications in the same manner as the light emitting/charge storage system described in connection with FIGS. 9 and 10, and the description of which is therefore omitted for the sake of brevity.

According, as described, the light emitting/charge storage device (the "Device") and light emitting/charge storage system (the "System") according to embodiments of the invention may advantageously be used in a wide variety of applications where illumination may be required, including display, lighting and phototherapy applications, and particularly useful where mechanical flexibility is required. In phototherapy applications for example, the Device and System may desirably provide at least one or more of the following advantages:

A. Cost and manufacturing: Certain embodiments of the OLED-based Device and System may cost less to manufacture than prior art phototherapy systems due to their inherently lower polymer materials cost, and abilities to comply to large scale printing type of roll-to-roll manufacturing. Further, as compared to prior art phototherapy systems, the System in some embodiments incorporate control, power, and user interface circuitry or electronics into a system-in-package, thereby lowering the assembly costs and simplifying the manufacturing process.

B. Dimensions, shape, and thickness: The polymeric nature of the Device and System in at least some embodiments may be formed into many convenient films, sheets, shapes, and surfaces lining various structures. For phototherapy applications, the Device and System may take form as patches, bandages, masks, garments, bed sheets, linings of tanning beds, incubators, for example. Additionally, the thickness of the constituent layers of the Device and System may be advantageously varied to comply with structural and power capacity requirements in a given application.

C. Robustness: As compared to the brittle and rigid nature of silicon light emitting diodes (LEDs) or other light emissive sources used in prior art phototherapy applications, the mechanically flexible qualities of the polymer materials used in certain embodiments may desirably provide robustness to the Device and System. Further, in at least some embodiments, hermetically sealing and encapsulating the Device and System may allow them to be desirably adapted for both short term disposable use and long term use, which may be greater than thirty (30) days, for example.

D. Integratability: In at least some embodiments, the Device and System may be configured to operate independently from external power supplies and/or rigid or non-portable control systems. In certain embodiments, the abilities to integrate the Device and System into a unitary stacked layered structure and to fabricate the same in polymer thin films ("thin profile") allow the Device and System to be particularly suitable for deployment or integration into various wearable solutions, such as clothing, body-suits and therapeutic blankets, for example.

E. Comfort: In at least some embodiments, the flexible, thin profile, and light-weight nature of the Device and System make them particularly suitable for integration into wearable phototherapy applications where comfort of use may be desired. Further, compliance with FDA skin biocompatibility, safety, and comfort requirements may be desirably achieved by simply tailoring the material properties of the encapsulant without having to alter the underlying Device and System or their fabrication process.

The exemplary embodiments herein described are not intended to be exhaustive or to limit the scope of the invention to the precise forms disclosed. They are chosen and described to explain the principles of the invention and its application and practical use to allow others skilled in the art to comprehend its teachings.

As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A light emitting/charge storage device comprising:
an organic light emitting diode (OLED) portion, comprising:
a first anode layer and a first cathode layer; and
an electroluminescent layer disposed at least partially between the first anode layer and the first cathode layer;
at least one polymeric charge storage portion electrically and physically connected with the OLED portion, the at least one polymeric charge storage portion comprising:
a second anode layer and a second cathode layer; and
an ionic polymer dielectric layer disposed at least partially between the second anode layer and the second cathode layer.

2. The light emitting/charge storage device according to claim 1, wherein the OLED portion is disposed at least partially on top of the at least one thin-film polymeric charge storage portion.

3. The light emitting/charge storage device according to claim 1, wherein the OLED portion further comprises at least one of: a hole transport layer and a hole injection layer disposed at least partially between the electroluminescent layer and the first anode layer.

4. The light emitting/charge storage device according to claim 1, wherein light emitting/charge storage device is mechanically flexible in at least one direction.

5. The light emitting/charge storage device according to claim 1, wherein the OLED portion further comprises an electron transport layer disposed at least partially between the electroluminescent layer and the first cathode layer.

6. The light emitting/charge storage device according to claim 1, wherein the OLED portion further comprises an insulating layer disposed at least partially on top of the first cathode layer.

7. The light emitting/charge storage device according to claim 1, wherein the OLED portion further comprises a substrate layer, the first anode layer being disposed at least partially on top of the substrate layer.

8. The light emitting/charge storage device according to claim 1 further comprising an insulating layer disposed at least partially on top of the second anode layer.

9. The light emitting/charge storage device according to claim 1, wherein the at least one polymeric charge storage portion comprises two or more thereof electrically connected to each other.

10. The light emitting/charge storage device according to claim 9, wherein the two or more polymeric charge storage portions are stacked substantially on top of each other.

11. The light emitting/charge storage device according to claim 10, further comprising an insulating layer disposed at least partially between the two or more polymeric charge storage portions.

12. The light emitting/charge storage device according to claim 1, wherein the OLED portion and the at least one polymeric charge storage portion are electrically connected to each other through one or more patterned conductive vias.

13. The light emitting/charge storage device according to claim 1, wherein the OLED portion and the at least one polymeric charge storage portion are electrically connected to each other through one or more printed electrical interconnects.

14. A light emitting/charge storage system comprising:
- a thin-film layered organic light emitting diode (OLED) portion;
- a thin-film layered charge storage portion electrically and physically connected with the thin-film layered OLED portion; and
- circuitry for providing one or more of: energy recharge, power regulation and system control functionality to the at least one thin-film layered charge storage portion.

15. The light emitting/charge storage system according to claim 14, wherein the circuitry comprises at least one of: thin-film transistor layers, unpackaged chips, and packaged modules integrated with one or more of the thin-film layered OLED portion and thin-film layered charge storage portion.

16. The light emitting/charge storage system according to claim 15, wherein at least a portion of the system is encapsulated in an encapsulant.

17. The light emitting/charge storage system according to claim 16, wherein the encapsulant comprises at least one material selected from the list comprising: polymers, thermoplastics, thermosets and elastomers.

18. The light emitting/charge storage system according to claim 16, wherein the encapsulant is mechanically flexible in at least one direction.

19. The light emitting/charge storage system according to claim 14, wherein the thin-film layered charge storage portion comprises a polymeric capacitor, comprising:
- an anode layer;
- a cathode layer; and
- an ionic polymer dielectric layer disposed at least partially between the anode layer and the cathode layer.

20. The light emitting/charge storage system according to claim 14, wherein the thin-film layered charge storage portion comprises a thin film battery.

* * * * *